United States Patent
Burkinshaw et al.

(10) Patent No.: US 6,551,321 B1
(45) Date of Patent: Apr. 22, 2003

(54) FLEXIBLE INTRAMEDULLARY NAIL

(75) Inventors: Brian D. Burkinshaw, Pflugerville, TX (US); Donald W. Dye, Pflugerville, TX (US); John L. Walker, Round Rock, TX (US); Steven Brown, Pflugerville, TX (US)

(73) Assignee: Centerpulse Orthopedics Inc., Austin, TX (US)

( * ) Notice: Subject to any disclaimer, the term of this patent is extended or adjusted under 35 U.S.C. 154(b) by 221 days.

(21) Appl. No.: 09/602,970

(22) Filed: Jun. 23, 2000

(51) Int. Cl.⁷ .................................. A61B 17/72
(52) U.S. Cl. ............................. 606/62; 606/64
(58) Field of Search .................. 606/60, 62, 63, 606/64, 67, 72, 61, 232

(56) References Cited

U.S. PATENT DOCUMENTS

| | | |
|---|---|---|
| 3,977,398 A | 8/1976 | Burstein |
| 4,446,857 A | 5/1984 | Otte et al. |
| 4,457,301 A | 7/1984 | Walker |
| 4,846,162 A | 7/1989 | Moehring |
| 5,034,012 A | 7/1991 | Frigg ..................... 606/62 |
| 5,053,035 A | 10/1991 | McLaren ................ 606/67 |
| 5,066,296 A | 11/1991 | Chapman et al. ......... 606/64 |
| 5,116,335 A | 5/1992 | Hannon et al. ........... 606/62 |
| 5,135,527 A | 8/1992 | Ender ..................... 606/62 |
| 5,201,735 A | 4/1993 | Chapman et al. ......... 606/67 |
| 5,281,225 A | 1/1994 | Vicenzi ................... 606/62 |
| 5,433,718 A | 7/1995 | Brinker ................... 606/62 |
| 5,489,284 A | 2/1996 | James et al. .............. 606/62 |
| 5,569,249 A | 10/1996 | James et al. .............. 606/62 |
| 5,855,579 A | 1/1999 | James et al. .............. 606/62 |
| 5,928,235 A | 7/1999 | Friedl ..................... 606/64 |
| 6,224,600 B1 * | 5/2001 | Protogirou ............... 606/63 |

OTHER PUBLICATIONS

Surgical Technique Brochure: "The Versatile Nail," undated.

* cited by examiner

*Primary Examiner*—David O. Reip
(74) *Attorney, Agent, or Firm*—Kenneth S. Barrow

(57) ABSTRACT

An orthopedic implant includes a pair of spaced apart end caps which are interconnected by a plurality of elongated flexible members. Each end cap includes an aperture formed therethrough for the use of a trochanteric guide wire for piloting the implant during trial insertion and final insertion into an intramedullary canal. At least one of the end caps includes a rounded end to enhance insertion. Preferably, the flexible members are bowed outwardly to provide a "bird-cage" configuration.

26 Claims, 3 Drawing Sheets

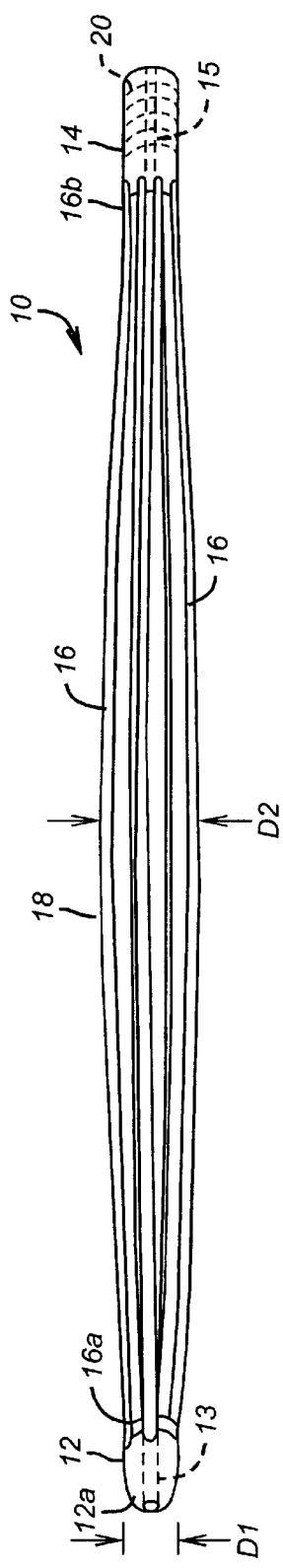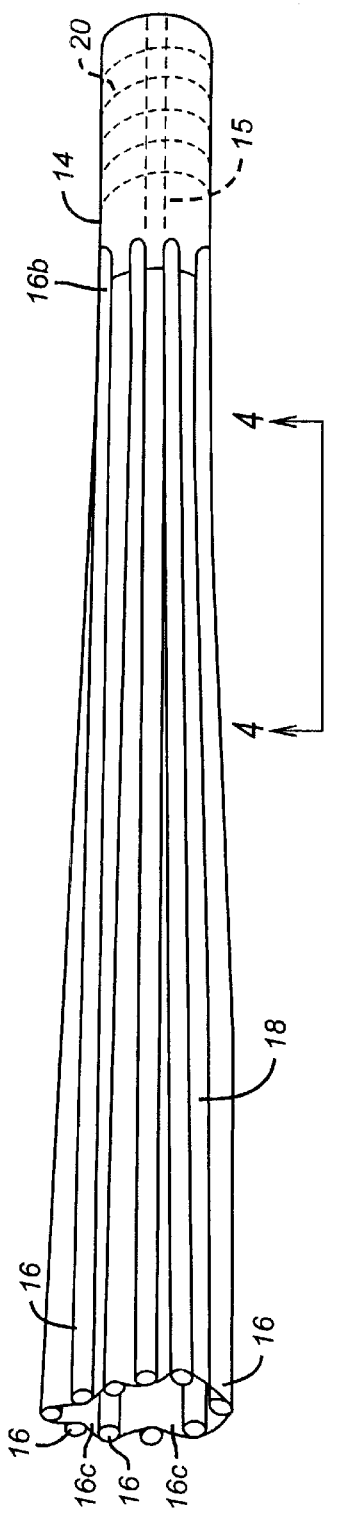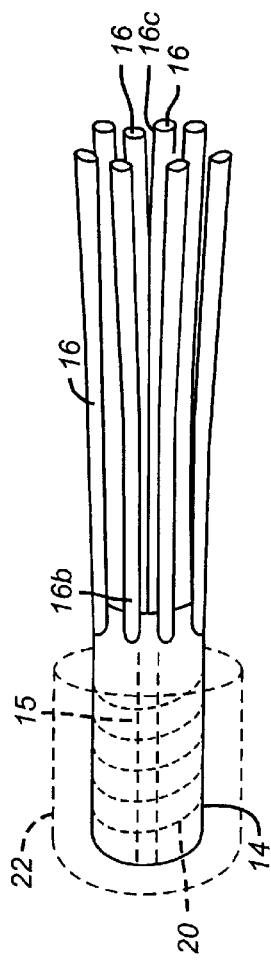

FLEXIBLE INTRAMEDULLARY NAIL

BACKGROUND

The disclosures herein related generally to orthopedic implants and more particularly to an intramedullary nail.

There is a need for a "limb salvage" method for treating metastatic tumor patients who had either suffered from a fractured limb, were in danger of suffering from a fractured limb due to voids in the bone structure, or were in need of internal limb stabilization resulting from actual or pending pathologic fracture of a limb. One common treatment described in the literature for these conditions is to retrograde fill the intramedullary (I-M) canal of the bone with bone cement and insert an I-M nail, bridging the defect, before the bone cement hardens. The reason for using a standard design I-M nail with cement is to provide stabilization and reinforce the limb around the void, deficient bone, or fracture site in order to prevent further deterioration. Without the use of cement for patients with these conditions, there is likely to be motion at the fracture site resulting in instability.

A common problem with this technique is that the I-M nail becomes lodged in the I-M canal before reaching full insertion. This is commonly the result of one or more causes such as: 1) the I-M rod selected becomes impinged at the fracture or bony defect site of the I-M canal; 2) most bones in the body have an anatomic bow (in one or more axis) that effectively reduces the diameter of the I-M canal through which a straight or non-flexible rod can pass without becoming immovably lodged prior to reaching the desired depth; and 3) due to a combination of the aforementioned conditions, the bone cement begins to harden before insertion of the rod is complete, thus preventing final seating of the device.

Another consideration is the application of an I-M rod as either a prophylactic treatment for the prevention of fracture or corrective trauma surgery for a long bone fracture for patients suffering front osteoporosis. It is known from literature that patients suffering from advanced stages of osteoporosis are more likely to fracture major bones sustained from simple trauma such as falling down. In such cases, surgeons may elect to use an I-M rod along with other stabilization techniques (i.e.: casting and/or cross-pinning) to achieve stabilization during healing. A device, used without bone cement, could serve this purpose, providing the same benefits to the surgeon as described in items 1 and 2 above. If needed, the device could still be removed at a later date.

Some of the known devices used for purposes mentioned above include U.S. Pat. No. 4,457,301 which describes an intramedullary multiple pin device for fixing fractures in the middle portion (diaphysis) of long bones. The multiple pins are resilient and held in a desired special arrangement by a flexible plastic core element.

U.S. Pat. No. 5,116,335 discloses an intramedullary device for use in internal fixation of a fracture transverse to the longitudinal axis of a long bone which includes a substantially rigid center rod having a plurality of longitudinal slots extending along the length thereof. One of a plurality of generally flexible outer rods is received and retained within one of the longitudinal slots and thereby extends outwardly from the center rod. Each outer rod has a retention section angulated from the longitudinal axis of the long bone which penetrates through and is retained by the cancellous bone thereby stabilizing the fracture at the distal and proximal ends of the long bone. In order to install the intramedullary device within the endosteal canal, each end of the generally flexible outer rods are coupled to one of a plurality of extension rods of an installation device. The generally rigid center rod is introduced through the central opening of the installation device and thus extends into the endosteal canal. As the center rod is moved into the endosteal canal, each of the outer rods is slidably engaged into one of the plurality of longitudinal slots of the center rod. This movement forces the cutting edge of each outer rod to penetrate through the cancellous bone and allows the retention section of the outer rods to be retained within the cancellous bone thereby stabilizing the fracture of the long bone.

In U.S. Pat. No. 5,135,527, an insert member for use in an impact hole leading into a medullary canal of a bone for treating a fracture by insertion of at least one bone nail into the medullary canal is disclosed. The insert member has a guide channel for receiving the proximal end of the bone nail, lateral openings and a pin for fixing the insert member in the impact hole, and a closure member for the proximal end of the guide channel. The closure member includes an abutment for the proximal end of the bone nail which allows limited reverse movement of the proximal end of the bone nail within the guide channel. The abutment may be a separate member attached to the closure member by a spring or the abutment may be a shaped projection extending forwardly from the closure member.

U.S. Pat. No. 5,281,225 discloses an intramedullary pin with a self-locking end for metadiaphyseal fractures, constituted by a proximal stub provided with means for fixing to the cortices; the ends of at least two curved and elastically deformable stems are axially rigidly associated with the stub, and the stems are adapted to expand elastically and to press with their tips the walls of the bone from the inside of the medullary canal.

Therefore, what is needed is a flexible intramedullary nail that allows for easier navigation through anatomic bows of the I-M canal during insertion, that can be piloted during trial insertion and final insertion, that allows for easy extrusion of bone cement into the body of the nail, and that can be used for stabilization in non-cemented applications.

SUMMARY

One embodiment, accordingly, provides a flexible intramedullary nail which reduces resistance to penetration within the intramedullary canal, which can be used with or without bone cement, and which meets the anatomic requirements of various bones in the human skeleton. To this end, an orthopedic implant includes a first end cap, a second end cap spaced apart from the first end cap, and a plurality of elongated flexible members interconnecting the first end cap and the second end cap.

A principal advantage of this embodiment is that the "birdcage configuration of the implant device is variably flexible for easier insertion through the anatomic bows of the intramedullary canal. The device may be varied in length, diameter and stiffness, and may be used with or without bone cement.

BRIEF DESCRIPTION OF THE DRAWING FIGURES

FIG. 1 is an isometric view illustrating an embodiment of a flexible intramedullary nail.

FIG. 2 is a partial isometric view of the intramedullary nail of FIG. 1.

FIG. 3 is another partial isometric view of the intramedullary nail of FIG. 1 including an adapter attached to an end cap.

DETAILED DESCRIPTION

Figure 4:
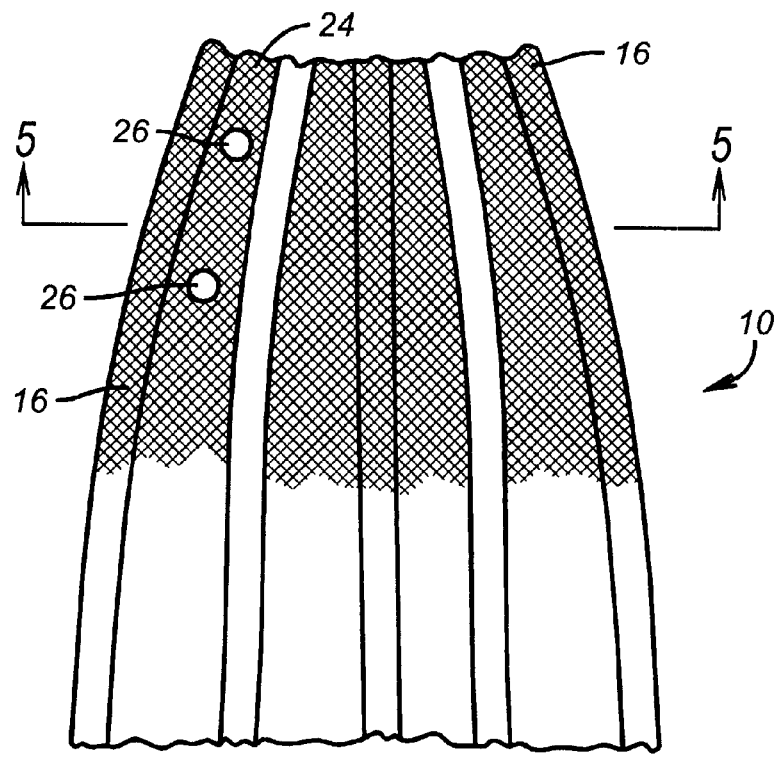
FIG. 4 is a partial side view of a section of the intramedullary nail including a mesh material, taken the line 4—4 of FIG. 2.

An orthopedic implant device such as a flexible intramedullary nail is generally designated 10 in FIGS. 1 and 2. Nail 10 includes a first end cap 12, a second end cap 14, and a plurality of elongated, individual flexible members 16 interconnecting the first end cap 12 and the second end cap 14. The flexible members 16 are preferably spaced apart or bowed outwardly to form a birdcage portion 18 between the end caps 12 and 14. As a result, the birdcage portion 18 has an expanded diameter. For example, each end cap 12 and 14 has a first diameter D1, and the birdcage portion has a diameter D2 which is about 33 percent greater than D1.

One of the end caps 12 includes a rounded end 12a. Each of the end caps 12 and 14 may include an aperture formed therethrough such as aperture 13 in end cap 12 and aperture 15 in end cap 14. However, in some applications only one of the end caps 12 may have an aperture. An end 16a of each flexible member 16 is attached to end cap 12, and an opposite end 16b of each flexible member 16 is attached to end cap 14.

End cap 14 may include a threaded portion 20 for receiving an adapter 22, FIG. 3. Adapter 22 is removably attachable to end cap 14 via threads 20. As a result, adapter 22 is attached to end cap 14 for use in driving the nail 10 into an intramedullary canal in a major skeletal member (not shown) such as a femur, tibia or humerus, for example. The expanded diameter birdcage portion 18 of the nail 10 provides a compressive engagement between the nail 10 and the walls of the intramedullary canal. Also, the rounded end 12a of end cap 12, FIG. 1, facilitates the passage of nail 10 through the intramedullary canal.

After the nail 10 is positioned as desired, the adapter 22 can be removed. Bone cement can be urged into the birdcage portion 18 of the nail 10 via the aperture 15 in end cap 14. The bone cement can exit the birdcage portion 18 through spaces 16c existing between each of the flexible members 16, see FIGS. 2 and 3.

Figure 5:
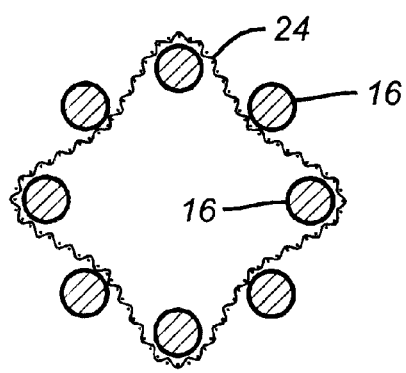
FIG. 5 is a cross-sectional view of a portion of the intramedullary nail taken long the line 5—5 of FIG. 4.

If desired, a more controlled exit of bone cement from bird cage portion 18 may be accomplished by the addition of a liner of a suitable mesh material 24, FIG. 4. Mesh material 24 may be retained on nail 10 adjacent the flexible members 16 by, for example, weaving the material 24 in and out of adjacent flexible members 16 as illustrated in FIG. 5. In addition, punctures 26 may be formed in mesh 24 at preselected locations to control and concentrate the exit of bone cement to certain defective areas of the skeletal member as decided by the surgeon.

Figures 6, 6A, 6B:
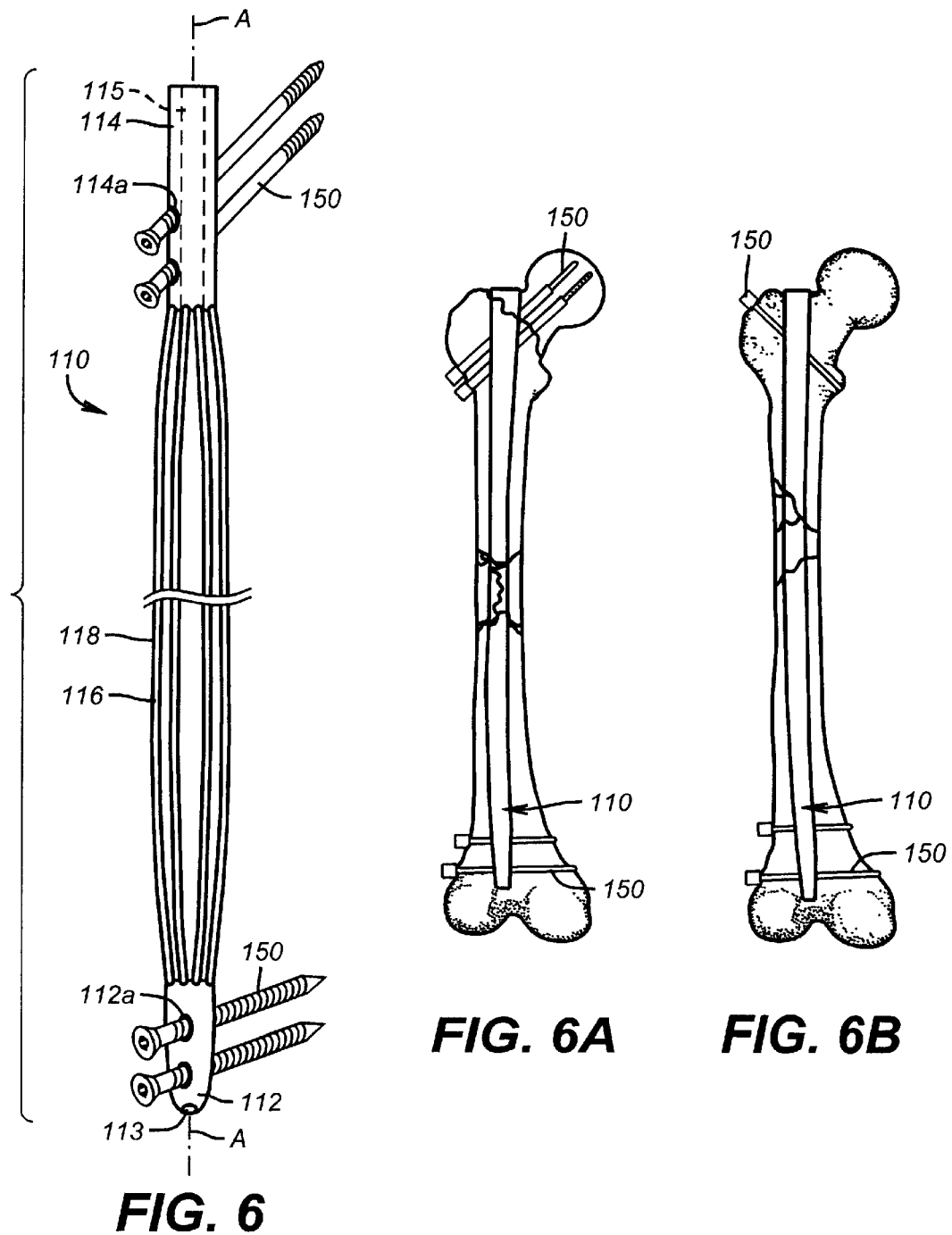
FIG. 6 is an isometric view of an embodiment of the intramedullary nail for use as an interlocking nail.
FIG. 6A and 6B illustrate examples of using the intramedullary nail as an interlocking nail.

In FIG. 6, an alternative embodiment illustrates a flexible intramedullary nail 110 for use as an interlocking nail. A first end cap 112 and a second end cap 114 each include a plurality of transversely extending apertures, 112a and 114a, respectively, in addition to a pair of axially extending apertures 113 and 115, respectively, extending along a centroidal axis A. The first end cap 112 and second end cap 114 are interconnected by flexible members 116 which are bowed outwardly to form a birdcage portion 118. The intramedullary nail 110 of this embodiment may be used as an interlocking nail when used in combination with well-known surgical screws 150 which extend through apertures 112a and 114a, see also FIGS. 6A and 6B.

In addition, the various embodiments of the flexible intramedullary nail disclosed herein may be inserted after cement is located in the intramedullary canal. Also, the flexible intramedullary nail may be inserted into a bone without cement. The flexible features of this intramedullary nail permit the nail to flex around obstructions in the intramedullary canal and provide the ability for the nail to accommodate anatomic anomalies.

In operation, flexible intramedullary nail 10 is formed to include a rounded first end cap 12 and second end cap 14 including a bone cement aperture 15 formed therethrough. The first and second end caps 12, 14, respectively, are interconnected by a plurality of flexible members 16 forming an expanded birdcage portion 18 which provides a bone cement reservoir in the nail 10. The end cap 14 includes threads 20 for receiving and retaining a removable adapter 22 which is used to drive nail 10 into a prepared intramedullary canal. When the nail 10 is positioned as desired in the canal, the adapter 22 is removed. Bone cement can then be urged into the birdcage portion 18 of nail 10 via the aperture 15 in end cap 14. The bone cement can exit the birdcage portion 18 by passing between the flexible members 16.

The mesh 24 may be added to the nail 10 and may include the punctures 26 for a more controlled and concentrated exit of the bone cement from the birdcage portion 18.

As a result, one embodiment provides an orthopedic implant including a first end cap, a second end cap spaced apart from the first end cap, and a plurality of elongated flexible members interconnecting the first end cap and the second end cap.

Another embodiment provides an intramedullary nail including a first end cap, a second end cap spaced apart from the first end cap, and a plurality of spaced apart flexible members interconnecting the first end cap and the second end cap to form a birdcage portion between the first and second end caps.

A further embodiment provides a flexible intramedullary nail including a first end cap having a first diameter, a second end cap having substantially the first diameter and a plurality of outwardly bowed flexible members interconnecting the first end cap and the second end cap such that the bowed members form a second diameter which is greater than the first diameter.

Major features of these embodiments provide an intramedullary nail constructed from an assembly of multiple rods, wires or filaments attached at both ends by end caps, at least one of which may be rounded at one end, to better facilitate conveyance through the I-M canal of a bone. The nail may be constructed from a plurality of materials including, but not limited to Stainless Steel, Titanium, any combination of alloys comprised from Titanium or Stainless Steel, such as Ti6Al4V, 300 series SS or CoCrMo, and/or materials such as any fiber filament bundle composites, etc. The number of rods, wires or filament bundles per assembly can range from as few as three to as many as nine, depending on the desired assembly properties. The rods, wires or filament bundles can be of variable lengths and diameters, ranging from 15 cm to 50 cm, and 75 mm to 4.5 mm, respectively. The overall diameter of the rod assembly at the ends can range from 5 mm to 24 mm. The overall length of the rod assembly can range from 18 cm to 55 cm. The end caps may include a through hole, to allow for the passage of a trochanteric wire to aid in the passage of the rod through the I-M canal of the bone and past any internal obstructions such as voids or fractures. The diameter of the through hole could be in a range between, but not limited to, 1.5 mm and 3.5 mm. One of the end caps would preferably have a rounded or ogive shaped tip intended as the leading end, and the opposite end cap would allow for attachment to a driving mechanism to facilitate controlled insertion of the device. The opposite end cap would also allow for the passage of bone cement. The assembly can be formed in such a way as to create an axially elongated ellipsoid, having a larger diameter in the center, in the relaxed condition. The diameter of the assembly could be as much as 33% greater in the center of its length. The advantage of the collapsible ellipsoid configuration is that this type of shape promotes a self-centering relationship between the nail and the I-M canal of the bone.

As it can be seen, the principal advantages of these embodiments are that the "birdcage" configuration of the body is variably flexible, allowing for easier navigation of the nail through anatomic bows of the I-M canal during insertion. Depending on with which bone the nail used, variable lengths, diameters and stiffness can be easily engineered to match the need. The flexibility of the nail body can be engineered for varying degrees of stiffness based upon the following factors: 1) material selection; 2) body diameter; 3) wire diameter; 4) length of wire; 5) wire cross-section and 6) number of wires used in the body. Just as in architectural designs, stiffness of a reinforced cement column such as this can be engineered to meet the anatomic requirements of various bones in the human skeleton.

A through-hole in both ends of the nail allows for the use of a trochanteric guide wire for piloting the nail during trial insertion or final insertion of the nail. The "birdcage" body design of the nail allows for easy extrusion of the bone cement into the body of the nail over its entire length. This provides some unique advantages over the existing I-M rod technology. The resulting combination "birdcage" and bone cement column is very similar to reinforced cement columns, such as that found in concrete structures; i.e.: bridges, buildings, etc. This reinforced column structure provides for the desired strength of the composite construction with the flexibility of the wire frame. Resistance to penetration within the bone's I-M canal is reduced because the internal pressure created by the insertion of the rod into the cement-filled bone is reduced when compared to a solid-walled I-M rod. The cement can easily flow into the void space between the wire rods in the body of the nail thus reducing the risk of pulmonary embolism, stroke, and other common adverse reactions associated with bone cements and this type of pressurizing procedure.

Another advantage of this design is the ability to use it for stabilization in a non-cemented application for the treatment of, or prophylaxis of fractures resulting from advanced osteoporosis. Simple adjustment in the design parameters for the wire/rods could result in the desired level of stiffness to achieve desired stability yet would still maintain adequate flexibility to allow for easier insertion than conventional I-M rods. This device could be inserted to achieve the necessary stability to allow proper healing in concert with other healing regimens to treat the osteoporosis, allowing for later removal, if needed. The device could also be configured as an interlocking nail, thus expanding its potential indications for use.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. An orthopedic implant comprising:
   a first end cap;
   a second end cap spaced apart from the first end cap; and
   a plurality of elongated flexible members interconnecting the first end cap and the second end cap, wherein at least one end cap has a rounded end, and each end cap includes an aperture formed axially therethrough.

2. The implant as defined in claim 1 wherein the end caps and flexible members are formed of biocompatible material.

3. The implant as defined in claim 1 including from three to nine flexible members.

4. The implant as defined in claim 1 wherein the flexible members are bowed outwardly between the first and second end caps.

5. The implant as defined in claim 4 wherein the end caps each have a first diameter and the bowed outward flexible members form a second diameter which is about 33 percent greater than the first diameter.

6. An intramedullary nail comprising:
   a first end cap;
   a second end cap spaced apart from the first end cap; and
   a plurality of spaced apart flexible members interconnecting the first end cap and the second end cap to form a birdcage portion between the first and second end caps, wherein at least one end cap has a rounded end, and each end cap includes an aperture formed therethrough.

7. The intramedullary nail as defined in claim 6 wherein the end caps and flexible members are formed of biocompatible material.

8. The intramedullary nail as defined in claim 6 including from three to nine flexible members, each flexible member being spaced apart from each other flexible member.

9. The intramedullary nail as defined in claim 6 wherein the flexible members are bowed outwardly between the first and second end caps, the end caps each having a first diameter, and the bowed outward flexible members forming a second diameter greater than the first diameter.

10. A flexible intramedullary nail comprising:
    a first end cap having a first diameter;
    a second end cap having substantially the first diameter; and
    a plurality of outwardly bowed flexible members interconnecting the first end cap and the second end cap such that the bowed members form a second diameter which is greater than the first diameter, wherein at least one end cap has a rounded end, and each end cap includes an aperture formed therethrough.

11. The flexible intramedullary nail as defined in claim 10 wherein the first end cap has a rounded end and the second end cap has an aperture formed therethrough, the second end cap also including means for receiving a removable adapter.

12. The flexible intramedullary nail as defined in claim 11 further comprising:
    a liner adjacent the flexible members for retaining bone cement, the liner including punctures formed therein for permitting controlled and concentrated exit of the bone cement.

13. The flexible intramedullary nail as defined in claim 11 further comprising:

a liner adjacent the flexible members for retaining bone cement, the liner being formed of a material which may be punctured for permitting a controlled and concentrated exit of the bone cement.

14. A method of reinforcing a skeletal member comprising the steps of:

forming a flexible intramedullary nail including a rounded first end cap and a second end cap including a bone cement aperture formed therein, the first and second end caps being interconnected by a plurality of elongated flexible members forming a bone cement reservoir;

attaching removable adapter to the second end cap;

driving the nail into an intramedullary canal of the skeletal member;

removing the adapter; and forcing bone cement through the bone cement aperture into the bone cement reservoir until the bone cement exits the body adjacent the flexible members.

15. The method as defined in claim 14 further comprising the step of:

providing a liner in the bone cement reservoir; and providing punctures in the liner, whereby the bone cement exits the bone cement reservoir via the punctures.

16. An orthopedic implant comprising:

a first end cap;

a second end cap spaced apart from the first end cap;

a plurality of elongated flexible members interconnecting the first end cap and the second end cap; and an aperture formed in each end cap, the aperture extending substantially transverse to a centroidal axis extending through each end cap.

17. The implant as defined in claim 16 wherein each end cap includes an aperture formed along the respective centroidal axis.

18. A method of reinforcing a skeletal member comprising the steps of:

forming a flexible intramedullary nail including a rounded first end cap and a second end cap, the first and second end caps being interconnected by a plurality of elongated flexible members;

attaching a removable adapter to the second end cap;

driving the nail into an intramedullary canal of the skeletal member; and removing the adapter.

19. A method of reinforcing a skeletal member comprising the steps of:

forming a flexible intramedullary nail including a rounded first end cap and a second end cap, the first and second end caps being interconnected by a plurality of elongated flexible members;

attaching a removable adapter to the second end cap;

inserting bone cement into an intramedullary canal of the skeletal member;

driving the nail into the intramedullary canal of the skeletal member; and removing the adapter.

20. An intramedullary nail, comprising:

a first end cap;

a second end cap spaced apart from the first end cap and having a plurality of transversely extending apertures adapted to receive a surgical screw; and a plurality of elongated flexible members interconnecting the first end cap and the second end cap.

21. The intramedullary nail of claim 20 wherein the first end cap includes a plurality of transversely extending apertures adapted to receive a surgical screw.

22. The intramedullary nail of claim 21 wherein the second end cap further includes an axially extending aperture.

23. The intramedullary nail of claim 22 wherein the first end cap further includes an axially extending aperture.

24. An intramedullary nail, comprising:

a first end cap;

a second end cap spaced apart from the first end cap;

a plurality of elongated flexible members interconnecting the first end cap and the second end cap; and a liner adjacent the flexible members, the liner being adapted to retain bone cement.

25. The intramedullary nail of claim 24 wherein the liner is a mesh material.

26. The intramedullary nail of claim 25 wherein the liner includes a plurality of punctures adapted to control concentration of the bone cement.

\* \* \* \* \*